United States Patent
Bsoul et al.

(10) Patent No.: US 10,213,152 B2
(45) Date of Patent: Feb. 26, 2019

(54) SYSTEM AND METHOD FOR REAL-TIME MEASUREMENT OF SLEEP QUALITY

(75) Inventors: Majdi Bsoul, Plano, TX (US); Lakshman S. Tamil, Plano, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 1255 days.

(21) Appl. No.: 13/396,520

(22) Filed: Feb. 14, 2012

(65) Prior Publication Data

US 2013/0046151 A1 Feb. 21, 2013

Related U.S. Application Data

(60) Provisional application No. 61/442,706, filed on Feb. 14, 2011.

(51) Int. Cl.
| | | |
|---|---|---|
| *A61B 5/0205* | (2006.01) | |
| *A61B 5/0452* | (2006.01) | |
| *A61B 5/00* | (2006.01) | |
| A61B 5/1455 | (2006.01) | |

(52) U.S. Cl.
CPC .......... *A61B 5/4806* (2013.01); *A61B 5/0205* (2013.01); *A61B 5/4815* (2013.01); *A61B 5/0022* (2013.01); *A61B 5/0024* (2013.01); *A61B 5/0452* (2013.01); *A61B 5/14551* (2013.01); *A61B 2560/045* (2013.01)

(58) Field of Classification Search
USPC ................................................. 600/300–301
See application file for complete search history.

(56) References Cited

U.S. PATENT DOCUMENTS

| | | | | | |
|---|---|---|---|---|---|
| 5,047,930 | A | * | 9/1991 | Martens | A61B 5/0476 128/920 |
| 5,299,118 | A | * | 3/1994 | Martens | A61B 5/0476 600/509 |
| 7,285,090 | B2 | * | 10/2007 | Stivoric | A61B 5/01 128/905 |
| 7,343,198 | B2 | * | 3/2008 | Behbehani | A61B 5/0456 600/509 |
| 7,462,150 | B1 | * | 12/2008 | Bharmi | A61B 5/02405 600/300 |
| 7,654,948 | B2 | * | 2/2010 | Kaplan | A61B 5/4809 600/26 |

(Continued)

*Primary Examiner* — Christopher A Flory
*Assistant Examiner* — Shirley X Jian
(74) *Attorney, Agent, or Firm* — Talem IP Law, LLP

(57) ABSTRACT

An embodiment of the invention is directed to a method for the real time monitoring and measurement of sleep quality of a subject comprising the steps of; obtaining information from the subject using sensory signals; analyzing the information contained within the signals using signal processing and artificial intelligence; and using the analyzed information to create a protocol to improve the sleep quality of the subject. Another embodiment of the invention is directed to a system for real time monitoring and measurement of sleep quality of a subject comprising: a means for obtaining sensory information from the subject; a means for transmitting the sensory information; a means for analyzing the sensory information; and a means for creating a protocol to improve the sleep quality of the subject.

20 Claims, 2 Drawing Sheets

(56) References Cited

U.S. PATENT DOCUMENTS

| | | | | |
|---|---|---|---|---|
| 7,959,567 B2* | 6/2011 | Stivoric | A61B 5/411 | 128/921 |
| 8,157,731 B2* | 4/2012 | Teller | A61B 5/01 | 128/921 |
| 8,348,840 B2* | 1/2013 | Heit | A61M 21/00 | 600/300 |
| 8,398,546 B2* | 3/2013 | Pacione | A61B 5/411 | 128/920 |
| 8,562,526 B2* | 10/2013 | Heneghan | A61B 5/0507 | 128/920 |
| 8,641,612 B2* | 2/2014 | Teller | A61B 5/01 | 600/300 |
| 8,708,904 B2* | 4/2014 | Stivoric | A61B 5/01 | 600/301 |
| 8,852,098 B2* | 10/2014 | Teller | A61B 5/01 | 600/301 |
| 8,968,196 B2* | 3/2015 | Teller | A61B 5/01 | 600/301 |
| 2004/0133081 A1* | 7/2004 | Teller | A61B 5/01 | 600/300 |
| 2004/0152957 A1* | 8/2004 | Stivoric | A61B 5/01 | 600/300 |
| 2005/0113650 A1* | 5/2005 | Pacione | A61B 5/411 | 600/300 |
| 2005/0267362 A1* | 12/2005 | Mietus | A61B 5/0205 | 600/429 |
| 2006/0041201 A1* | 2/2006 | Behbehani | A61B 5/0456 | 600/521 |
| 2006/0111635 A1* | 5/2006 | Todros | A61B 5/0402 | 600/484 |
| 2006/0235315 A1* | 10/2006 | Akselrod | A61B 5/02405 | 600/509 |
| 2006/0253004 A1* | 11/2006 | Frisch | G06F 19/3418 | 600/300 |
| 2007/0032733 A1* | 2/2007 | Burton | A61B 5/02405 | 600/509 |
| 2007/0213624 A1* | 9/2007 | Reisfeld | A61B 5/0402 | 600/504 |
| 2008/0161654 A1* | 7/2008 | Teller | A61B 5/01 | 600/300 |
| 2008/0161655 A1* | 7/2008 | Teller | A61B 5/01 | 600/300 |
| 2008/0167536 A1* | 7/2008 | Teller | A61B 5/01 | 600/301 |
| 2008/0167537 A1* | 7/2008 | Teller | A61B 5/01 | 600/301 |
| 2008/0167538 A1* | 7/2008 | Teller | A61B 5/01 | 600/301 |
| 2008/0167539 A1* | 7/2008 | Teller | A61B 5/01 | 600/301 |
| 2008/0171919 A1* | 7/2008 | Stivoric | A61B 5/01 | 600/301 |
| 2008/0171920 A1* | 7/2008 | Teller | A61B 5/01 | 600/301 |
| 2008/0171921 A1* | 7/2008 | Teller | A61B 5/01 | 600/301 |
| 2008/0171922 A1* | 7/2008 | Teller | A61B 5/01 | 600/301 |
| 2008/0275309 A1* | 11/2008 | Stivoric | A61B 5/411 | 600/300 |
| 2009/0131764 A1* | 5/2009 | Lee | A61B 5/0484 | 600/301 |
| 2009/0131803 A1* | 5/2009 | Heneghan | A61B 5/4812 | 600/484 |
| 2009/0203972 A1* | 8/2009 | Heneghan | A61B 5/0507 | 600/301 |
| 2010/0049008 A1* | 2/2010 | Doherty | A61B 5/0476 | 600/301 |
| 2011/0190594 A1* | 8/2011 | Heit | A61M 21/00 | 600/301 |
| 2013/0046151 A1* | 2/2013 | Bsoul | A61B 5/4806 | 600/301 |
| 2013/0158367 A1* | 6/2013 | Pacione | E04F 13/06 | 600/301 |
| 2013/0158368 A1* | 6/2013 | Pacione | E04F 13/06 | 600/301 |
| 2014/0206955 A1* | 7/2014 | Stivoric | A61B 5/01 | 600/301 |
| 2014/0213855 A1* | 7/2014 | Teller | A61B 5/01 | 600/301 |
| 2014/0213856 A1* | 7/2014 | Teller | A61B 5/01 | 600/301 |
| 2014/0213857 A1* | 7/2014 | Teller | A61B 5/01 | 600/301 |
| 2014/0221769 A1* | 8/2014 | Teller | A61B 5/01 | 600/301 |
| 2014/0221770 A1* | 8/2014 | Teller | A61B 5/01 | 600/301 |
| 2014/0221774 A1* | 8/2014 | Teller | A61B 5/01 | 600/301 |
| 2014/0221784 A1* | 8/2014 | Pacione | E04F 13/06 | 600/301 |
| 2014/0221791 A1* | 8/2014 | Pacione | A61B 5/7455 | 600/301 |
| 2014/0222174 A1* | 8/2014 | Teller | A61B 5/01 | 700/91 |
| 2014/0223406 A1* | 8/2014 | Teller | A61B 5/01 | 717/100 |
| 2014/0223407 A1* | 8/2014 | Teller | A61B 5/01 | 717/100 |
| 2014/0257055 A1* | 9/2014 | Pacione | E04F 13/06 | 600/301 |
| 2014/0257540 A1* | 9/2014 | Pacione | E04F 13/06 | 700/91 |
| 2014/0324459 A1* | 10/2014 | Barfield | G06F 19/3418 | 705/3 |
| 2014/0330094 A1* | 11/2014 | Pacione | A61B 5/411 | 600/301 |
| 2014/0342328 A1* | 11/2014 | Pacione | E04F 13/06 | 434/236 |
| 2015/0302722 A1* | 10/2015 | Berezhnyy | A61B 5/04012 | 340/565 |
| 2016/0120464 A1* | 5/2016 | Lau | A61B 5/7267 | 600/324 |
| 2017/0173262 A1* | 6/2017 | Veltz | A61M 5/1723 | |
| 2017/0265765 A1* | 9/2017 | Baumann | G06F 19/00 | |

* cited by examiner

SYSTEM AND METHOD FOR REAL-TIME MEASUREMENT OF SLEEP QUALITY

CROSS-REFERENCES TO RELATED APPLICATIONS

This application claims the benefit under 35 U.S.C. § 119(e) of U.S. Provisional Patent Application Ser. No. 61/442,706 filed Feb. 14, 2011, which is incorporated herein by reference in its entirety as if fully set forth herein.

STATEMENT REGARDING FEDERALLY-SPONSORED RESEARCH OR DEVELOPMENT

None

FIELD OF INVENTION

The field of the invention is directed to the assessment of sleep quality.

BACKGROUND OF THE INVENTION

About 70 million Americans suffer from a sleep problem; nearly 60 percent of them have a chronic disorder. The quantity of sleep that a person gets is not as important as quality. Sleep is primarily a restorative process that influences the homeostatic regulation of the autonomic, neuroendocrine, and immune systems. The behavioral habits, sleep related breathing disorders such as apnea, drugs such as sleeping pills and alcoholic beverages can suppress certain stages of sleep leading to poor sleep quality or even sleep deprivation that have serious effects on individual's health and wellness and lead to various medical problems like cognitive impairment and heart.

Obstructive Sleep Apnea (OSA) is a common disorder that affects about 4% of the general population. People with sleep apnea literally stop breathing repeatedly during their sleep, often for a period of 10-30 seconds and as many as hundreds of times during one night. The frequent arousals and the inability to achieve or maintain the deeper stages of sleep can lead to excessive daytime sleepiness, non-restorative sleep, automobile accidents, personality changes, decreased memory, erectile dysfunction (impotence), and depression. OSA has also been linked to angina, nocturnal cardiac arrhythmias, myocardial infarction and stroke.

There are several currently existing solutions for diagnosing OSA. The primary method for diagnosing OSA currently is to have the patient undergo a sleep study, known as Polysomnography (PSG). A polysomnogram typically records a minimum of eleven channels of various bio-signals requiring a minimum of 22 wire attachments to the patient in a specialized sleep laboratory with attended personnel. Obstructive sleep apnea is diagnosed if the patient has an apnea index (apneic episodes per hour) of greater than 5. Polysomnography is a very costly procedure and does not lend itself to application outside of a medical facility.

Specialized devices using $SpO_2$ oximetry sensors that detect apnea intervals have also been used. These systems have proprietary $SpO_2$ wired sensors and the detected intervals tend to combine multiple apnea episodes. Thus, individual apnea episodes are not detectable using $SpO_2$ oximetry sensors.

Other devices include commercial sleep monitors using brain waves (EEG), ECG and proprietary devices and protocols, which do not satisfactorily detect apneic episodes.

SUMMARY OF THE INVENTION

An embodiment of the invention is directed to a method for the real time monitoring and measurement of sleep quality of a subject comprising the steps of; obtaining information from the subject using sensory signals; analyzing the information contained within the signals using signal processing and artificial intelligence; and using the analyzed information to create a protocol to improve the sleep quality of the subject.

An embodiment of the invention is directed to a system for real time monitoring and measurement of sleep quality of a subject comprising: a means for obtaining sensory information from the subject; a means for transmitting the sensory information; a means for analyzing the sensory information; and a means for creating a protocol to improve the sleep quality of the subject.

DESCRIPTION OF EXEMPLARY EMBODIMENTS

Figure 1:
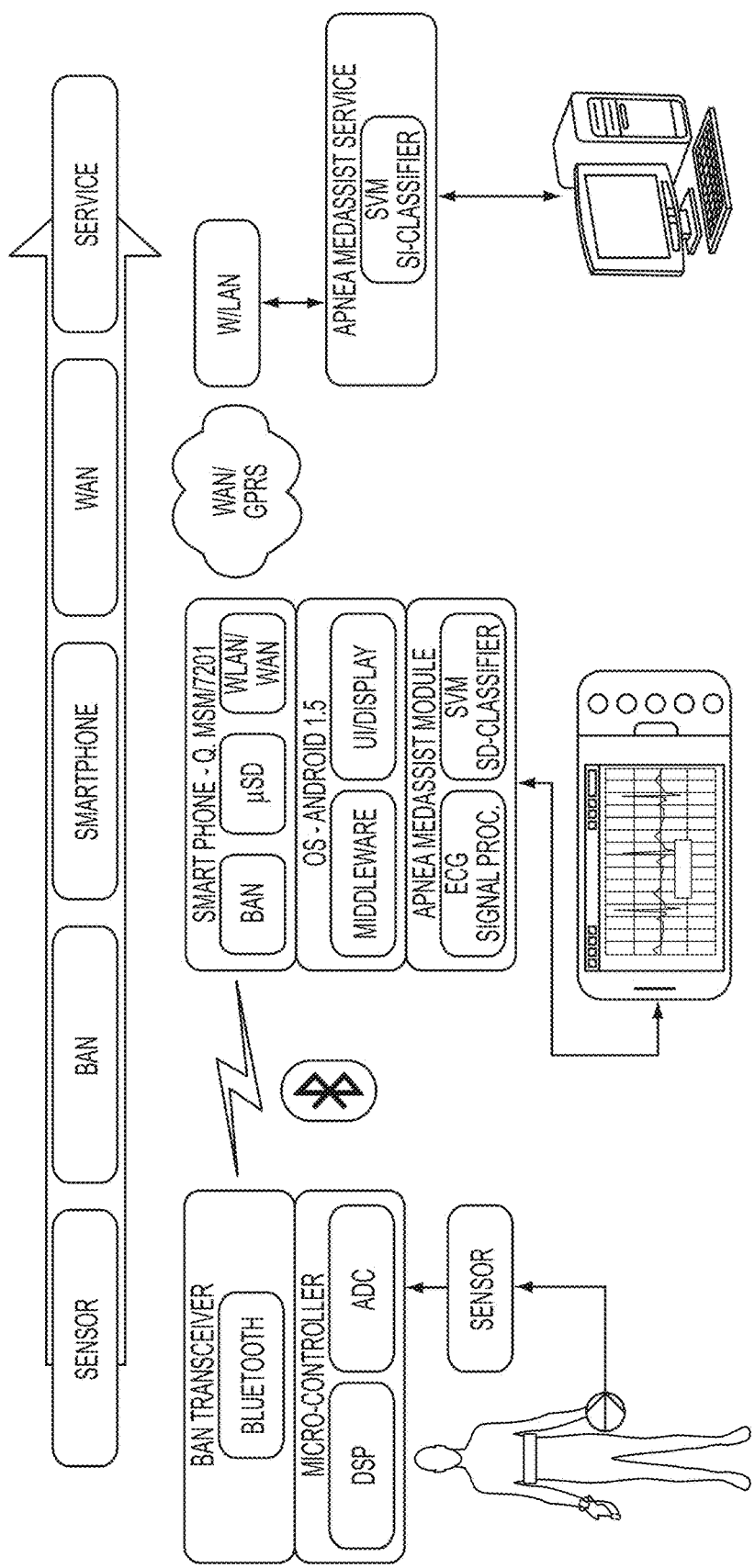
FIG. 1 represents an architecture of a system in accordance with an embodiment of the invention.

An embodiment of the invention is directed to develop a simpler system for assessing OSA in patients before, during and after medical treatments. The real-time OSA detection is critical in perioperative monitoring, which includes assessing the presence and severity of sleep apnea to avoid complications during and after surgery.

An embodiment of the invention is directed to using single-channel ECG measurements to monitor apnea episodes in a subject. Using a single-channel ECG measurement reduces the complexity of the diagnostic test and enables patients to better monitor physiological changes corresponding to changes in sleep apnea severity.

Other embodiments of the invention are directed to the use of physiological signals derived from electroencephalograms (EEGs), oxygen saturation measurements ($SpO_2$), electrooculograms (EOGs), electromyograms (EMGs), respiratory monitors, audio signals and/or video signals.

An embodiment of the invention is directed to using support vector machine (SVM) as a method for apnea pattern classification. SVM maps data into a high-dimensional space and find a separating hyperplane with maximal margin. SVM classifier (SVC) models assist in the automatic classification of apnea episodes according to patient criteria—the existence of prior annotated sleep apnea data for the subject or for another subject, by matching his physical attributes—and/or device connectivity and processing capabilities.

An embodiment of the invention is directed to screening apnea on the basis of a one minute segment of data rather than treating the entire recording as a single segment. This measurement segment length is chosen to reduce the number of hidden actual episodes within the selected time interval.

Another embodiment of the invention is directed to real-time screening instead of the offline screening that currently exists in prior methods.

A further embodiment of the invention is directed to assessment of apnea severity or apnea/hypopnea index on the basis of the number of apnea episodes detected over the total segments, as opposed to the posterior probability of SVM outputs.

An additional embodiment of the invention is directed to two SVM classifier models, subject-independent and subject-dependent, for apnea detection.

A further embodiment of the invention is directed to a system that provides fully automated signal processing, feature extraction and apnea SVM classifier in a smartphone or similar device.

An embodiment of the invention is directed to the transmission of the data from the smartphone to a doctor's office.

In another embodiment of the invention, the apnea data is saved on the subject's smartphone for future review and reference. In certain embodiments, once the data is received by the subject's smartphone, the smartphone alerts the subject to the presence of the data.

An embodiment of the invention is directed to a system comprising a sensor or a plurality of sensors for acquiring ECG, oxygen saturation level in blood, and other vital signals connected wirelessly or using wires to a smart phone or a smart phone like device, an internet downloadable software residing on the smart phone or a smart phone like device performing signal processing and decision making based on artificial intelligence.

In an embodiment, the vital signal can be transmitted to a compute cloud, where the software for signal processing and decision making reside and the computed results of sleep quality and apnea indices are transferred back to a smart phone or a smart phone like device.

In an embodiment, context information obtained automatically in the device is used along with machine learning algorithms in improving the predictive accuracy of sleep quality or sleep apnea.

In an embodiment, self-learning algorithms work with machine learning algorithms in increasing the predictive accuracy of the sleep quality or sleep apnea.

In a further embodiment, the vital signals can be transmitted to a nearby computer where the signal processing and decision support software resides.

FIG. 1 represents the architecture of a system in accordance with an embodiment of the invention. As shown in FIG. 1, one or more sensors are removably attached to a subject's body. The sensors may be located on a waist belt worn by the subject and/or a wrist-held sensor removably attached to the finger tip of the subject. The signals from the sensor are transmitted from the sensor via a body area network (BAN) to a smartphone or smartphone-like device. In an embodiment of the invention, the smartphone or smartphone-like device contains the proprietary software that analyzes the signals transmitted by the sensor. The data analysis results in the development of a protocol to assist the subject with the improvement of sleep quality and/or treatment of sleep apnea.

In certain embodiments of the invention, the protocol is transmitted via a wide area network (WAN) to a medical service or a doctor's office, and saved on a computer at this location.

In some embodiments of the invention, there are two types of physiological sensors used: a single lead ECG and a finger tip oximeter. The system comprises three modules: a signal processing module, a feature extraction module and a classifier module. In the case of ECG, the measurements with a sampling period of 4 msec are segmented into 1 min epoch and passed through the signal processing module which uses an automated wavelet based analysis to perform denoising, detrending and detection of characteristics points:

QRS complex, P and T waves. The morphology changes in the ECG waves allow deriving a signal proportional to the respiratory movement. T-wave is used to extract the surrogate respiratory signal and in cases where T-wave cannot be detected, R-wave amplitude was used. Both time and frequency based parameters are used to extract features. A full feature set of 111 elements and a reduced feature set of 19 elements are used in apnea classification. The full set is used for implementation in a compute cloud and the reduced set is used for a standalone implementation in a smartphone.

In the case of oximetry signal, the signal processing module cleans up the signal and detects the characteristic points such as the oxygen desaturation (ODI) indices. Using time only parameters, a full feature set of 20 elements and a reduced feature set of 3 elements are derived for use in classification. The reduced feature set is used in stand alone implementation in smartphones whereas the full feature set is used in compute cloud implementation.

Support Vector Machine (SVM) classifiers have been used to classify every one minute epoch as an apnea or a nonapnea episode. SVM is a powerful discriminative method for pattern classification. The full feature extraction module and SVM classifiers are implemeted in the "google cloud" whereas the extraction of reduced feature set and the signal processing module are implemented in a 3G/4G smart phone.

As a step towards preparing the system for patient trial, the system was validated using the Physionet Apnea-ECG database. The results obtained for the ECG sensor and the Oximetry sensor are shown in Table 1 and Table 2 respectively. For both the sensors, the accuracy obtained is better than 90% when full set of features are used for classification, whereas for the reduced set, the accuracy is just little below 90%.

TABLE 1

| | Full Set | | | Reduced Set | | |
|---|---|---|---|---|---|---|
| C | Sens (%) Spec (%) | Acc (%) | F-Score (%) | Sens (%) Spec (%) | Acc (%) | F-Score (%) |
| 0.5 | 90.02 91.73 | 91.09 | 90.86 | 88.35 90.72 | 89.83 | 89.52 |
| 1 | 89.80 92.00 | 91.18 | 90.88 | 88.03 90.97 | 89.86 | 89.48 |
| 2 | 89.62 91.98 | 91.11 | 90.78 | 87.99 91.06 | 89.91 | 89.50 |
| 8 | 89.02 92.14 | 90.99 | 90.55 | 87.69 91.18 | 89.97 | 89.40 |
| 32 | 89.12 92.35 | 91.16 | 90.70 | 87.35 91.14 | 89.72 | 89.21 |

TABLE 2

| | Sensitivity | specificity | Accuracy |
|---|---|---|---|
| Full set | 0.90 | 0.94 | 0.92 |
| Reduced Set | 0.94 | 0.94 | 0.94 |

Figure 2:
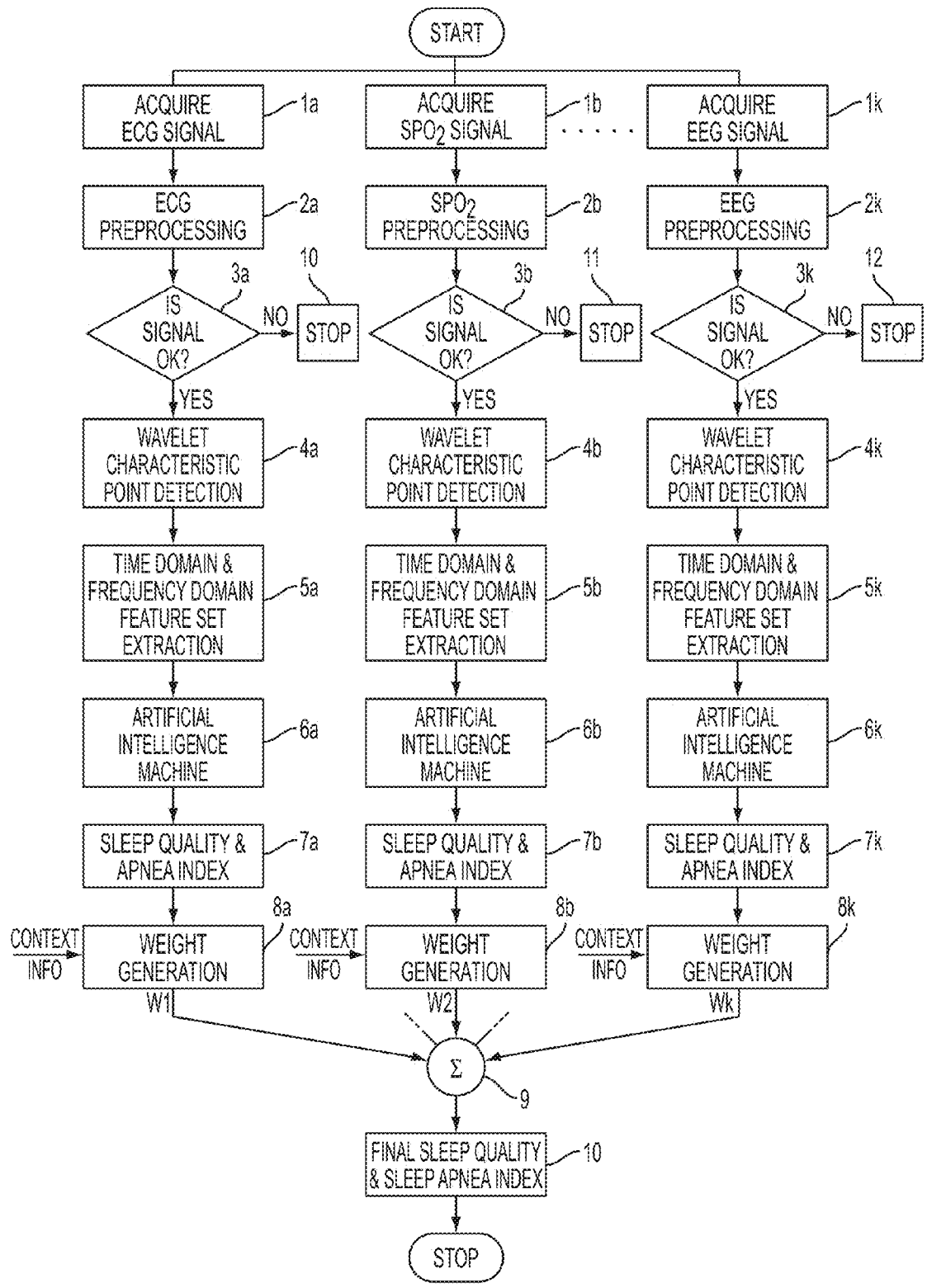
FIG. 2 represents a flow chart showing a sequence of computations in accordance with an embodiment of the invention.

An embodiment of the invention is described herein using FIG. 2. "a" to "k" represent various physiological signal sensors such as ECG, $SpO_2$, EEG, audio, and video signals.

Step 1a: A single lead ECG in the form of a strap with three wires, or a pod worn around the neck with three patches or a single patch with three contact wires acquires the ECG signal.

Step 1b: Same as Step 1a except that the ECG is replaced by an oximeter.

Step 1k: Same as Step 1a except that the ECG replaced by an EEG sensor.

Step 2a: The ECG preprocessing is done either using hardware or software or a combination of both. In a hardware configuration, a FPGA or an application specific integrated circuit can be used. In the software configuration, for example a wavelet algorithm implemented in a general processor like TI MSP 430 can be used.

Step 2b: Same as step 2a but ECG replaced by an oximeter.

Step 2k: Same as step 2a but ECG replaced by an EEG sensor.

Step 3a: Decision is made on the quality of the ECG signal acquired. An algorithm that computes the signal quality is used. If the signal is good enough, then the signal acquisition continues otherwise the signal acquisition is terminated or started again and a report is displayed on the patient's console accordingly.

Step 3b: Same as step 3a but ECG replaced by an oximeter.

Step 3k: Same as step 3a but ECG replaced by an EEG sensor.

Step 4a: The characteristics points of ECG such as P, QRS complex and T waves are detected here. For example, this can be done using second generation undecimated lifting wavelet Transform (ULWT). The ULWT has reduced computational cost compared to other techniques such as FIR implementation. The ULWT provides the characteristics points.

Step 4b: Same as step 4a but ECG replaced by an oximeter.

Step 4k: Same as step 4a but ECG replaced by an EEG sensor.

Step 5a: Extraction of time domain and frequency domain feature set and ECG derived breathing information (EDR) are all carried out. For example various parameters in both time and frequency domain are computed using Fast Fourier Transform (FFT), Decimated Wavelet Transform (DWT) using Daubechies 4 wavelet and Statistical computations. In one of the embodiments, a total of 111 parameters to computer Apnea index and 112 parameters to compute sleep quality indices were used. In an another embodiment, a reduced set of 19 elements extracted using F1 score measures was used.

Step 5b: Same as step 5a but ECG replaced by an oximeter.

Step 5k: Same as step 5a but ECG replaced by an EEG sensor.

Step 6a: An artificial intelligence based machine is used for decision making. This involves training the machines using positive and negative examples. For example the training can be accomplished using sleep databases available or from physician scored sleep study data. Artificial intelligence machine for example can be based on Support Vector Machines (SVM). Support vector machine classifiers simply perform classification by constructing an n-dimensional hyperplane that optimally separates the data into two classes. SVM finds the optimum separating hyperplane with maximum distance from nearest training patterns. Those nearest training vectors are called support vectors.

Step 6b: Same as step 6a but ECG replaced by an oximeter.

Step 6k: Same as step 6a but ECG replaced by an EEG sensor.

Step 7a: The sleep apnea index and/or sleep quality indices are computed here. The ECG signal divided into 30 s or 1 minute epochs are used in computing the feature vectors which when fed to the artificial intelligent machine makes a determination whether that epoch is an apnea event or a non apnea event. In an another embodiment for measuring the sleep quality, the SVM is a multi class machine and it makes a determination on the staging of the sleep. It is classified as Wake/sleep state, REM/nonREM state, SWS/nonSWS state etc. An overall sleep index namely sleep efficiency, deep sleep efficiency and sleep onset latency is computed here from the results provided by the artificial intelligent classifier.

Step 7b: Same as step 7a but ECG replaced by an oximeter.

Step 7k: Same as step 7a but ECG replaced by an EEG sensor.

Step 8a: Depending on the context information provided either manually or by the context sensors, and from the accuracy of the ECG data, a weight is generated for the ECG data.

Step 8b: Same as step 8a but ECG replaced by an oximeter.

Step 8k: Same as step 8a but ECG replaced by an EEG sensor.

Step 9: One embodiment of the invention uses data from a single sensor in providing sleep apnea index or sleep quality index. The sensor with highest weight is used and is based on the context. In another embodiment, a plurality of sensors are used. The results from the plurality of sensors are combined using data fusion techniques using the weights computed from context and accuracy.

Step 10: Using data fusion techniques, a high overall accuracy is achieved.

Sleep Quality and Apnea Assessment:

A feature of the inventive system reduces the cost and setup time. It uses a wireless smartphones as a cost-effective platform, which allow farther reach of this monitor. Embodiments of the invention utilize Android, I-Phone and other known smartphone operating systems.

A feature of the inventive system uses only single channel ECG measurements to reduce the complexity of the diagnostic test and enables patients to better monitor physiological changes corresponding to changes in sleep apnea severity and sleep quality.

A feature of the inventive system uses both RR tachogram and ECG-derived respiratory extracted signals using only one ECG channel sensor to provide a high predictivity.

A feature of the invention is the real-time monitoring of sleep apnea/sleep quality, which is based on a per-minute segment that detected apnea episodes on a more granular interval allowing it to be more accurate towards the actual AHI. Used in critical real-time settings like perioperative monitoring which includes assessing the presence and severity of sleep apnea to avoid complications during and after surgery. Also, real-time apnea monitoring can provide instantaneous results for any associated medical treatment such as feedback for CPAP pressure adjustments.

The inventive system can use prior apnea sleep data that was annotated by sleep experts to customize apnea monitor for the actual subject, hence; will have better predictivity and accuracy. The system can use prior sleep staging data that was annotated by sleep experts to customize sleep monitor for the actual subject, hence; will have better predictivity and accuracy.

The inventive system can communicate with the server in a real-time (every minute) to run a more accurate detection classifier and also report data or trigger other alerting mechanism for ambulatory type applications.

The inventive system has flexible update mechanism for:

Working with any available Bluetooth sensor with no proprietary interface;

Moving from server mode to standalone, once expert sleep apnea annotated data and expert sleep staging annotated data is available for subject;

Switching communication from Wi-Fi or cellular 3G data connectivity, allowing clinical or home based applications; and Upgrading software and used classifier models.

The Practical Utility of the Invention is Varied and Includes:

Hospital or Clinical Sleep Apnea Monitoring:

The patient can be monitored for sleep apnea even if the patient was not diagnosed previously with sleep apnea, because it is estimated that more that 85% of subjects with sleep apnea disorder are not diagnosed. This is in connection to the critical health risks that are accompanied during perioperative periods (admission, anesthesia, surgery, and recovery).

Sleep Apnea Patients Under Continuous Positive Airway Pressure (CPAP) Treatment (and Other Variations):

The patients who are diagnosed with sleep apnea and under the PAP-variants treatment can use this system to get a feedback on the correctness of the use of their treatment. In some instances the patient does not get the actual reduction in the apnea episodes because of malfunction or incorrectly applying the PAP treatment. This means that the side effects of sleep apnea will accumulate and the feedback while being treated will give the patient better assessment on the progress of his treatment.

Sleep Apnea Patients Side Effects:

Having a more affordable and less intrusive system will allow sleep apnea subjects with moderate severity or even other subjects to assess the effect of used medications or other therapies on their sleep apnea trends.

Sleep Disorders:

The number of health care providers committed to sleep studies is inadequate given the number of Americans who experience these disorders. Evidence indicates that the majority of people who have a sleep disorder go undiagnosed and untreated. For example, at least 75 percent of those who suffer from sleep apnea remain undiagnosed. Using only single channel ECG measurements reduces the complexity of the diagnostic test and enables patients to better monitor physiological changes corresponding to changes in sleep quality.

Sleep Quality Related Side Effects:

Having a more affordable and less intrusive system will allow subjects to assess the effect of used medications or other therapies on their sleep quality. Drugs such as sleeping pills and alcoholic beverages can suppress certain stages of sleep leading to poor sleep quality or even sleep deprivation that have serious effects on individual's health and wellness and lead to various medical problems like cognitive impairment and heart.

Additional Advantages Include:

High Degree of Accuracy of Obstructive Sleep Apnea (OSA) Episodes:

Uses a detection method with high predictivity based on Support Vector Machines classifiers. It achieves a classification F-measure of 90% and a sensitivity of 96% for the subject-independent SVM classifier.

Uses Both Heart Rate Variability (HRV) RR-Tachogram and the Surrogate ECG-Derived Respiration Signal (EDR):

A total of 111 features (time and spectral-domain) are extracted which increase the predictability of the apnea episodes.

Adaptable Architecture Between Standalone and Client-Server:

To work in home settings as well as integrate with clinical or hospital based server remotely. The system can communicate with the server to run a more accurate detection classifier and also report data or trigger other alerting mechanism for ambulatory type applications.

Uses Either General Adult Subject-Independent SVC Model or Subject-Dependent SVC Model:

The use of several SVM classifiers (SVC) models to automatically classify apnea episodes according to patient criteria based on the existence of prior reference sleep apnea data for the subject or for another subject matching his physical attributes, and/or device connectivity and processing capabilities.

Optimized and Realtime Signal Processing Based on 1-Minute Epoch Interval:

It includes multi-resolution wavelet analysis implemented on smartphones with reduced computational cost and achieves shorter epoch intervals. That enabled it to report a detected AHI (Apnea/Hypopnea Index) that is very close to the actual AHI. This also is critical in perioperative monitoring and can provide instantaneous results for any associated medical treatment such as feedback for CPAP pressure adjustments.

Ease of Use by Patients:

In terms of application user interface or setup of single-channel ECG sensor. Also, simple runtime options allow users to switch between the SVC models or connectivity capabilities.

Uses Both Heart Rate Variability (HRV) RR-Tachogram and the Surrogate ECG-Derived Respiration Signal (EDR):

A total of 113 features (time and spectral-domain) are extracted which increase the predictability of the sleep efficiency measures.

Adaptable Architecture Between Standalone and Client-Server:

To work in home settings as well as integrate with clinical or hospital based server remotely. The system can communicate with the server to run a more accurate detection classifier and also report data or trigger other alerting mechanism for ambulatory type applications.

Uses Either General Adult Subject-Independent SVC Model or Subject-Dependent SVC Model:

The use of several SVM classifiers (SVC) models to automatically classify sleep states according to patient criteria based on the existence of prior reference sleep staging data for the subject or for another subject matching his physical attributes- and/or device connectivity and processing capabilities.

Optimized and Realtime Signal Processing Based on Selected Epoch Interval:

It includes multi-resolution wavelet analysis implemented on smartphones with reduced computational cost and achieves shorter epoch intervals.

It will be appreciated that the above description for clarity has described embodiments of the invention with reference to different functional units and processors. However, it will be apparent that any suitable distribution of functionality between different functional units or processors may be used without detracting from the invention. For example, functionality illustrated to be performed by separate processors or controllers may be performed by the same processor or controllers. Hence, references to specific functional units are only to be seen as references to suitable means for providing the described functionality rather than indicative of a strict logical or physical structure or organization.

The invention can be implemented in any suitable form including hardware, software, firmware or any combination of these. The invention may optionally be implemented at least partly as computer software running on one or more data processors and/or digital signal processors. The elements and components of an embodiment of the invention may be physically, functionally and logically implemented in any suitable way. Indeed the functionality may be implemented in a single unit, in a plurality of units or as part of other functional units. As such, the invention may be implemented in a single unit or may be physically and functionally distributed between different units and processors.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term comprising does not exclude the presence of other elements or steps.

Furthermore, although individually listed, a plurality of means, elements or method steps may be implemented by e.g. a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category but rather indicates that the feature is equally applicable to other claim categories as appropriate. Furthermore, the order of features in the claims do not imply any specific order in which the features must be worked and in particular the order of individual steps in a method claim does not imply that the steps must be performed in this order. Rather, the steps may be performed in any suitable order. In addition, singular references do not exclude a plurality. Thus references to "a", "an", "first", "second" etc do not preclude a plurality.

What is claimed is:

1. A method for real time monitoring and measurement of sleep quality of a subject comprising:
    receiving, at a smartphone, a sensor signal corresponding to an electrocardiogram (ECG) from a subject and context information from one or more contextual sensors;
    analyzing, at the smartphone or a server, information contained within the sensor signal using signal processing and artificial intelligence, the analyzing comprising:
       segmenting the sensor signal corresponding to the ECG into signal segments of a specified epoch; and
       for each signal segment:
          detecting a set of characteristic points from the signal segment;
          extracting a feature set of elements from the signal segment using the set of characteristic points, time-based parameters, and frequency-based parameters, wherein the time-based parameters comprise ECG derived respiration (EDR) time series and RR time series, and the frequency-based parameters comprise EDR time series and RR time series; and
          classifying the signal segment as containing an apnea event or not containing the apnea event according to the extracted feature set, wherein classifying the signal segment comprises training a classifier with both self-learning algorithms and machine learning algorithms, the training including using the context information obtained automatically by the one or more contextual sensors and including optimizing the classifier for the subject through continued use by the subject of a device providing the sensor signal such that accuracy increases for classifying apnea events occurring for the subject; and
    outputting, via the smartphone, a sleep quality index of the subject based on at least one signal segment that has been classified as containing the apnea event or not containing the apnea event, wherein the sleep quality index is a total number of apnea events over an amount of sleep time.

2. The method according to claim 1, further comprising:
    receiving, at the smartphone, at least one signal selected from an electroencephalogram signal, a respiratory monitor signal, an electromyogram signal, an electrooculogram signal, a microphone signal, a video camera signal, and an oxygen saturation signal; and
    analyzing, at the smartphone or the server, information contained within the at least one signal; and combining results of the analyzing of the information contained within the at least one signal with results of the analyzing of the information contained within the sensor signal corresponding to the ECG.

3. The method according to claim 1, further comprising: outputting an alert indicating an identification of the sleep apnea event in response to classifying a particular signal segment as containing the apnea event or not containing the apnea event.

4. The method according to claim 1, further comprising:
    classifying the signal segment as a particular stage of sleep; and
    indicating overall sleep index of the subject based on at least one segment that has been classified having the particular stage of sleep,
    wherein the classifier is optimized for the subject through continued use by the subject of the device providing the sensor signal such that accuracy increases for classifying the stage of sleep for the subject.

5. The method according to claim 1, wherein the specified epoch is between 30 seconds to 1 minute, inclusive.

6. The method according to claim 1, wherein detecting the set of characteristic points comprises performing an automated wavelet based analysis for QRS complex, P wave, and either T wave or R-wave characteristic points.

7. The method according to claim 1, wherein extracting the feature set comprises:
    extracting, at the server, a full feature set of elements from the signal segment.

8. The method according to claim 1, wherein extracting the feature set comprises:
    extracting, at the smartphone, a reduced feature set of elements from the signal segment.

9. The method according to claim 1, wherein classifying the signal segment comprises using a support vector machine (SVM) classifier as the artificial intelligence.

10. The method according to claim 1, further comprising receiving, at the smartphone, a photoplethysmogram signal from an oximeter, and analyzing, at the smartphone or the server, information contained within the photoplethysmogram signal by at least:
    segmenting the photoplethysmogram signal into photoplethysmogram signal segments of the specified epoch; and for each photoplethysmogram signal segment:
    detecting characteristic points from the photoplethysmogram signal segment; and
    extracting a corresponding feature set for the photoplethysmogram signal segment using the characteristic points and time-based parameters for the photoplethysmogram signal segment.

11. The method according to claim 10, wherein extracting the corresponding feature set for the photoplethysmogram signal segment comprises:
    extracting, at the server, a full feature set of elements from the photoplethysmogram signal segment.

12. The method according to claim 10, wherein extracting the corresponding feature set for the photoplethysmogram signal segment comprises:
    extracting, at the smartphone, a reduced feature set of elements from the photoplethysmogram signal segment.

13. The method according to claim 10, wherein detecting the characteristic points comprises detecting oxygen desaturation indices.

14. A system for real-time measurement of sleep quality, comprising:
    a computing system having stored thereon computer software that, when executed by a processor of the computing system, directs the computing system to:
    receive a sensor signal comprising sensory information corresponding to at least an electrocardiogram (ECG) and context information from one or more context sensors;
    segment the sensor signal into signal segments of a specified epoch; and
    for each signal segment:
        detect a set of characteristic points from the signal segment;
        extract a feature set of elements from the signal segment using the set of characteristic points, time-based parameters, and frequency-based parameters, wherein the time-based parameters comprise ECG derived respiration (EDR) time series and RR time series, and the frequency-based parameters comprise EDR time series and RR time series; and
        classify the signal segment as containing an apnea event or not containing the apnea event according to the extracted feature set, wherein the computer software further directs the computing system to train a classifier used to classify the signal segment with both self-learning algorithms and machine learning algorithms, the training including using context information obtained automatically by the one or more context sensors and including optimizing the classifier for the subject through continued use by the subject of a device providing the sensor signal such that accuracy increases for classifying apnea events occurring for the subject; and
    output a sleep quality index of the subject based on at least one signal segment that has been classified as containing the apnea event or not containing the apnea event, wherein the sleep quality index is a total number of apnea events over an amount of sleep time.

15. The system according to claim 14, wherein the computing system comprises a server, wherein the computer software that directs the computing system to extract the feature set of elements directs the server to extract a full feature set of elements.

16. The system according to claim 14, wherein the computing system comprises a smartphone, wherein the computer software that directs the computing system to extract the feature set of elements directs the smartphone to extract a reduced feature set of elements.

17. The system according to claim 14, wherein the computer software that, when executed by the processor of the computing system, further directs the computing system to:
    classify the signal segment as a particular stage of sleep; and
    indicate overall sleep index of the subject based on at least one segment that has been classified having the particular stage of sleep,
    wherein the classifier is optimized for the subject through continued use by the subject of the device providing the sensor signal such that accuracy increases for classifying the stage of sleep for the subject.

18. The system according to claim 14, wherein the specified epoch is between 30 seconds to 1 minute, inclusive.

19. The system according to claim 14, wherein the computer software that directs the computing system to detect the set of characteristic points directs the computing system to perform an automated wavelet based analysis for QRS complex, P wave, and either T wave or R-wave characteristic points.

20. The system according to claim 14, further comprising:
    one or more sensors including a sensor providing the ECG; and
    a body area network receiving sensory information from the one or more sensors and transmitting the sensory information for receipt by the computing system.

* * * * *